United States Patent [19]

Nozawa et al.

[11] Patent Number: 5,328,826
[45] Date of Patent: Jul. 12, 1994

[54] IMMUNOCHEMICAL DETECTION OF HUMAN UTERINE ENDOMETRIAL CANCER CELL

[75] Inventors: Shiro Nozawa, 2-7-21-101, Motoazabu, Minato-ku, Tokyo, Japan; Katsumi Tsukazaki, Yamato; Motoko Kawamoto, Tokyo, all of Japan

[73] Assignees: Mochida Pharmaceutical Co., Ltd.; Shiro Nozawa, both of Tokyo, Japan

[21] Appl. No.: 855,880

[22] Filed: Mar. 23, 1992

[30] Foreign Application Priority Data

Mar. 22, 1991 [JP] Japan .................................. 3-059135

[51] Int. Cl.$^5$ .................... G01N 33/574; G01N 33/53
[52] U.S. Cl. ...................................... 435/6; 435/7.23; 435/7.92; 435/967; 435/973; 436/64; 436/518; 436/8; 436/813
[58] Field of Search .................. 435/7.23, 7.92, 967, 435/973, 6; 436/501, 64, 518, 8, 813

[56] References Cited

FOREIGN PATENT DOCUMENTS 2-113894  4/1990  Japan .

OTHER PUBLICATIONS

Lifschitz-Mercer et al., *Cancer*, vol. 59, No. 8, pp. 1494–1499, 1987, Abstract Only.
Farhood et al., *Human Pathology*, vol. 22, No. 3, pp. 224–230, 1991, Abstract Only.
*Basic & Clinical Immunology*, 4th edition, (Stites, et al., editors), Lange Medical Publications, Los Altos, California, pp. 351–356, 1982.
Nozawa et al., "A monoclonal antibody (MSN-1) against a newly established uterine endometrial cancer cell line (SNG-II) and its application to immunohistochemistry and flow cytometry," *American Journal of Obstetrics and Gynecology*, vol. 161, No. 4, Oct. 1989, pp. 1079–1086.
Iwamori et al., "Monoclonal Antibody-Defined Antigen of Human Uterine Endometrial Carcinomas Is Le," *J. Biochem.*, vol. 105, pp. 718–722, 1989.
Nozawa et al., "Production of Monoclonal Antibody Against a Newly Established Human Endometrial Cancer Cell Line SNG-II," *ACTA Obst. Gynaec. Jpn.*, vol. 39, No. 4, pp. 559–566, 1987.

*Primary Examiner*—Toni R. Scheiner
*Attorney, Agent, or Firm*—Burns, Doane, Swecker & Mathis

[57] ABSTRACT

A method of screening for the endometrial cancer cells in a endometrial cell specimen is disclosed. The method involves determining the amount of an endometrial cancer associated antigen relative to the sample amount by immunologically detecting and comparing the levels of the endometrial cancer associated antigen and a substance present in human cells in a substantially constant amount.

12 Claims, 5 Drawing Sheets

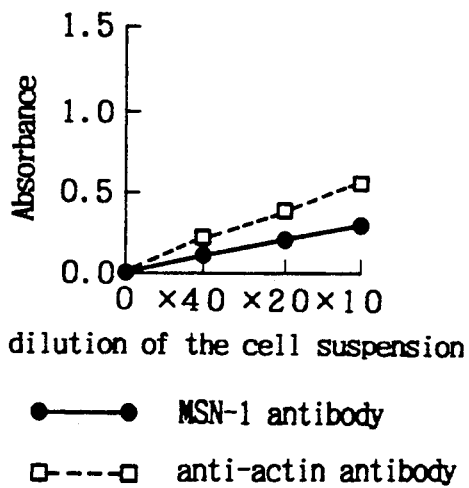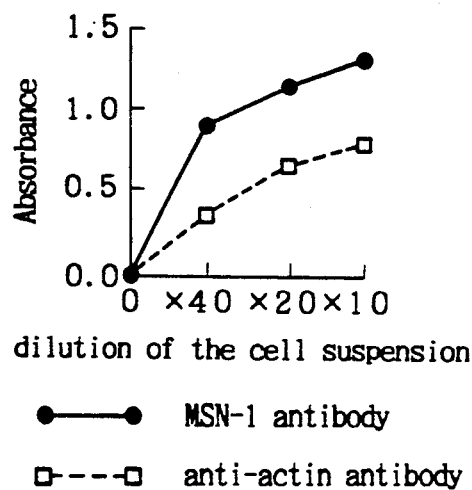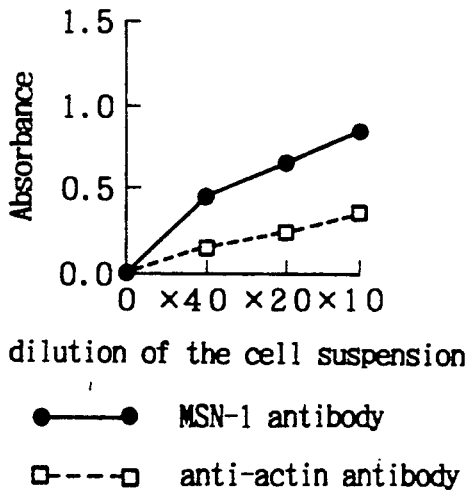

F I G. 3(a)
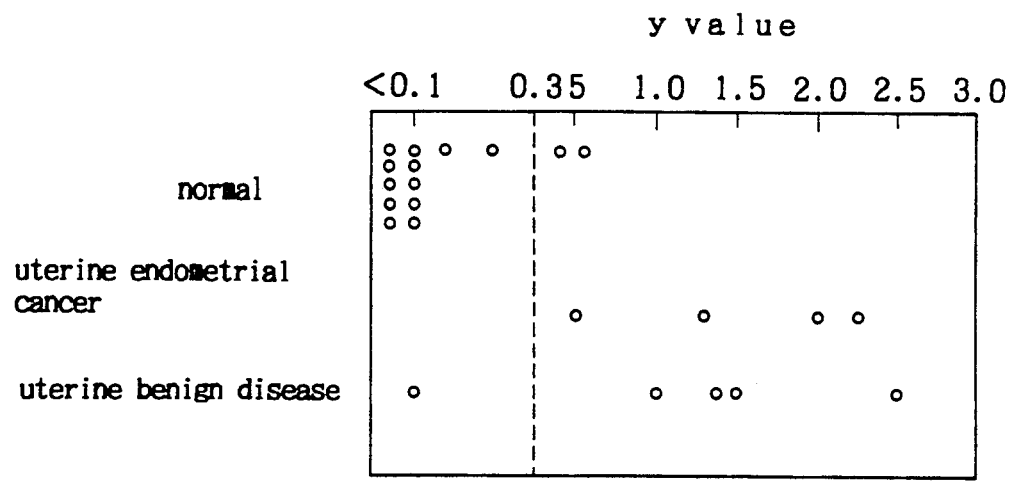
F I G. 3(b)
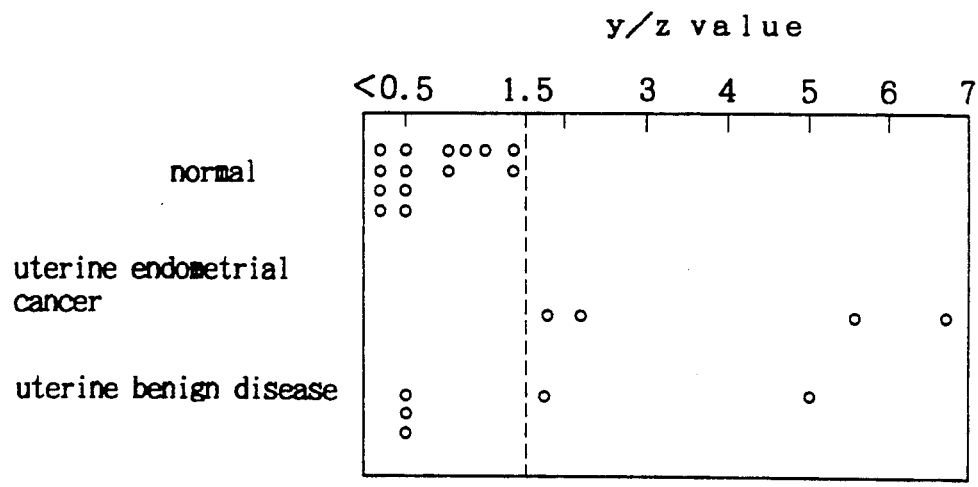
F I G. 3(c)
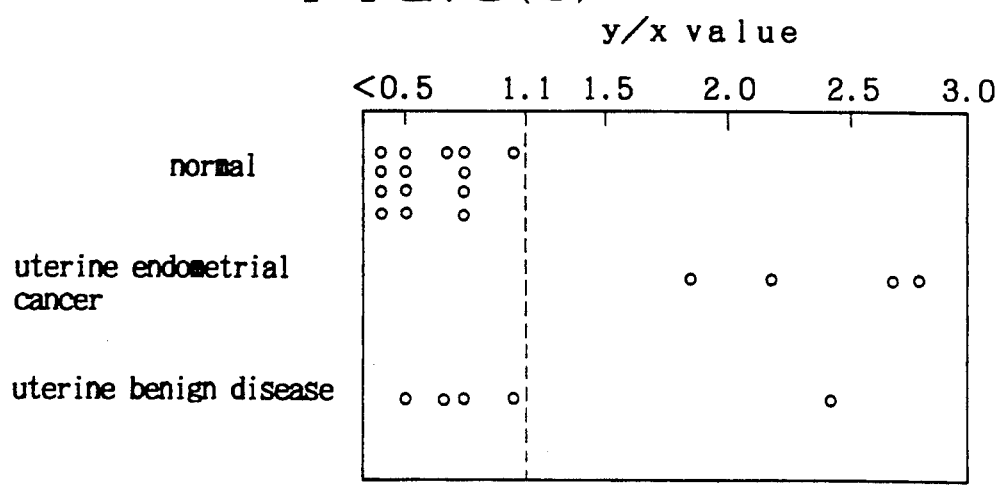

IMMUNOCHEMICAL DETECTION OF HUMAN UTERINE ENDOMETRIAL CANCER CELL

BACKGROUND OF THE INVENTION

This invention is directed to a process for immunochemically detecting uterine endometrial cancer cells in a uterine endometrial cell or endometrial tissue specimen.

Uterine endometrial cancer is increasing in Japan with westernization of eating habits and prolongation of people's lives. Today, endometrial cancer accounts for 10 to 20% of all uterine cancers. In consideration of such conditions, an item directed to a medical examination of the uterine endometrial cancer was included in the Law of Health and Medical Service System for the Aged in Jun. 1987 to spread the medical examination of the uterine endometrial cancer by law so that the cancer may be detected at an early stage.

Today, the medical examination of the uterine endometrial cancer is mainly carried out by means of cytodiagnosis, which has proved to be quite useful. The cytodiagnosis, however, requires a high skill. In addition, since most of the uterine endometrial cancer is an adenocarcinoma, discrimination between benign and malignant cell specimens on the bases of conventional morphological criteria has often been quite difficult. Therefore, there is a strong demand for a convenient, accurate process which is capable of handling a large number of specimens in a short period so that the process may be used for group examinations and mass screenings.

Immunohistochemical staining by utilizing a highly specific monoclonal antibody is a widely employed technique, and use of such a monoclonal antibody which specifically reacts with a tumor cell has been considered to be quite useful for accurately discriminating between benign and malignant cell specimens. In view of such conditions, Nozawa et al. produced a monoclonal antibody designated MSN-1, which is highly reactive with the uterine endometrial cancer cell (see Nozawa et al., Acta Obst. Gynaec. Jpn., 39, 559–566, 1987). This monoclonal antibody was applied to immunohistochemical staining of tissue specimens collected from uterine cavity of both normal people and patients suffering from the endometrial cancer, whereby more than 90% of the specimens collected from the endometrial cancer patients turned out to be positive while the normal specimens were scarcely stained (see Nozawa et al., American Journal of Obsterics and Gynecology, 161, 1079–1086, 1989). Such an immunohistochemical staining, however, depends on subjective criteria, and the results are often determined as false positive. Development of an improved detection method is therefore desired.

Further investigation of the above mentioned monoclonal antibody, MSN-1, indicated that the monoclonal antibody recognizes a sugar chain of a neutral glycolipid in the endometrial cancer cell, and that the reaction site is located at least on cell surface. In consideration of such an indication, the monoclonal antibody, MSN-1 was applied to flow cytometry, whereby the possibility of differentiating the endometrial normal cells from the cancer cells was indicated. Since the data provided by the flow cytometry is highly objective, it was concluded that the diagnosis of the uterine endometrial cancer by means of the flow cytometry would be useful (Nozawa et al., American Journal of Obsterics and Gynecology, 161, 1079–1086, 1989, supra). This method, however, requires complicated techniques as well as expensive equipment. Also, this method is incapable of examining a large number of specimens in a short period.

In addition to the problems as described above which are specific to the diagnosis of the uterine endometrial cancer, immunochemical detection generally suffers from the problem as described below.

In general, when a target substance such as a tumor marker in blood is measured and the result is determined whether it is positive or negative, namely, whether the measurement is within a normal range or not, a cut off value or a reference value is preliminarily set, and the results are determined by referring to such a value. However there are some false positive cases, wherein the tumor marker concentration in blood is high even though the sample has been collected from a normal volunteer or a patient suffering from a benign disease, and wherein the high measurement may not necessarily indicate a cancer. Various factors are estimated to be the causes of such a phenomenon including deficiency of the specificity of the antibody used and nonspecific reaction due to interfering components in the specimen.

This was also found to be the case with the diagnosis of the uterine endometrial cancer using the monoclonal antibody, MSN-1.

It was found that the monoclonal antibody, MSN-1 sometimes reacts with normal endometrial cells as well as endometrial cells of a benign endometrial disease, although the degree of the reaction was weak. Also, the labelled substance used is expected to adsorb nonspecifically. As a consequence, there were found some rare cases wherein the signal intensity indicated by the labelling agent of the labelled substance was high in spite of the absence of the endometrial cancer cell.

The cut off value is generally determined either statistically on the basis of distribution of the measurements of normal, benign disease and cancer cases, or in accordance with clinical utility.

A value equivalent to a cut off value would also be necessary for the detection of the endometrial cancer cell from endometrial cells collected from the uterine cavity. It is, however, quite difficult to collect a constant volume of the endometrial cells or tissue from the uterine cavity, and consequently, the quantity of the cells or tissue which is examined would be quite different from sample to sample. Therefore, the cut off value cannot be simply set on the basis of the signal intensity indicated by the labelling agent of the labelled substance.

This invention was developed in consideration of such a state of the art, and therefore, an object of the present invention is to provide an improved process for immunochemically detecting a human endometrial cancer cell by utilizing a monoclonal antibody which has a highly specific immunoreactivity to the endometrial cancer cell, and by simultaneously measuring two substances in the specimen and relatively evaluating the thus obtained measurements. Another object of the present invention is to provide a process which is capable conveniently, objectively, and accurately of determining the presence or the absence of the uterine endometrial cancer cell in the specimen.

In consideration of the problems associated with the diagnosis of the uterine endometrial cancer as mentioned above, the inventors of the present invention have made an intensive study to overcome such problems and developed a process by which any one can conveniently, accurately, and objectively detect endometrial cancer cell without requiring any special skill or equipment. In particular, the inventors attempted to more adequately set the cut off value.

First, the inventors decided to employ a monoclonal antibody which has a high reactivity to the uterine endometrial cancer cell, such as antibody, MSN-1, for the detection of the endometrial cancer cell, and to allow for the monoclonal antibody to react with the uterine endometrial cell specimen examined, which is immobilized on a carrier. It was also decided to use a known labelling agent for the detection.

Secondly, since an adequate setting of the cut off value is critical for more accurately determining the result of the cytodiagnosis, a means for setting the cut off value was investigated.

More illustratively, the inventors attempted to determine the total number of the cells (or an index for the total cell number) in the specimen, and to determine the ratio of number of the cells (or an index for the cell number) detected by using the antibody against the endometrial cancer cell per unit number of the cells, and then, set the cut off value on the basis of the thus determined ratio.

Typical methods for directly measuring the total number of the cells in the specimen include use of a hemocytometer and Coulter counter. It is, however, difficult to adopt such methods for the diagnosis of the uterine endometrial cancer since the number of the cells in the specimen collected from the uterine cavity is quite small.

It is also difficult to use protein content in disrupted or solubilized cells as an index for the total number of the cells in the specimen since quantitative analysis of the protein is complicated. Consequently, a more convenient process would be required for a group examination and mass screening wherein a large number of specimens must be quickly handled.

In view of such conditions, the inventors of the present invention decided to use quantity a substance which is generally present in human cells in a substantially constant amount as an index corresponding to the cell number or the quantity of the disrupted cells in the specimen, and carried out a quantitative measurement of such a substance by means of an immunochemical analysis similar to the direct detection of the uterine endometrial cancer cells. It was then confirmed that the quantity of the substance which is generally present in human cells in a substantially constant amount may be used as an index corresponding to the cell number or the quantity of the cell lysate in the specimen.

On the bases of the above-described findings, it was then found out that the presence or the absence of the uterine endometrial cancer cell in the specimen may be determined by, in the first place, immunochemically measuring a value corresponding to the quantity of the endometrial cancer cell in the specimen using the monoclonal antibody such as the antibody, MSN-1 which is highly reactive to the uterine endometrial cancer cell to measure the quantity of antigen which binds to such an antibody, as well as a value corresponding to the quantity of the substance which is generally present in human cells in a substantially constant amount, and in the next place, either simply comparing the thus obtained values, or calculating a ratio of the values and evaluating the ratio by referring to a preliminarily set cut off value to determine the presence or the absence of the uterine endometrial cancer cell in the specimen. It was also found that, by using this process, any one can conveniently, objectively, and accurately detect the uterine endometrial cancer cell without requiring any special technique or equipments.

The present invention has been completed on the bases of such findings.

According to first aspect of the present invention, there is provided a process for detecting a human uterine endometrial cancer cell by using a monoclonal antibody having a highly specific immunoreactivity to the human uterine endometrial cancer cell, comprising the steps of (a) preparing a specimen by collecting endometrial cells and/or endometrial tissue from the cavity of the uterus, and optionally disrupting the collected cells and/or the tissue, (b) immobilizing a predetermined amount of said specimen on two or more reaction areas on one or more carriers, (c) adding a labelled monoclonal antibody prepared by binding a labelling agent either directly or indirectly to said monoclonal antibody, and a labelled substance B prepared by binding a labelling agent either directly or indirectly to a substance B which is reactive to a substance A which is generally present in human cells, to different areas of said reaction areas onto which said specimen had been immobilized, respectively, to allow for said immobilized specimen to react with said labelled monoclonal antibody and with said labelled substance B, respectively, (d) washing said carrier to remove said labelled monoclonal antibody and said labelled substance B which failed to bind to said immobilized specimen, (e) measuring signal intensities y and x of said labelling agents of said labelled monoclonal antibody and said labelled substance B, which had been bound to said immobilized specimen, respectively, and (f) determining the presence or absence of the uterine endometrial cancer cell in the specimen by evaluating the signal intensity y indicated by the labelling agent of said labelled monoclonal antibody in relation to the signal intensity x indicated by the labelling agent of said labelled substance B.

This method may be referred to as Assay method I in the following description.

According to second aspect of the present invention, there is provided a process for detecting a human uterine endometrial cancer cell by using a monoclonal antibody having a highly specific immunoreactivity to the human uterine endometrial cancer cell, comprising the steps of (a) preparing a specimen by collecting endometrial cells and/or endometrial tissue from the cavity of the uterus, and optionally disrupting the collected cells and/or the tissue, (b) immobilizing a predetermined amount of said specimen on two or more reaction areas on one or more carriers, (c) adding said monoclonal antibody and a substance B which is reactive to a substance A which is generally present in human cells to different areas of said reaction areas onto which said specimen had been immobilized to allow for said immobilized specimen to react with said monoclonal antibody and with said substance B, respectively, (d) adding a labelled substance C prepared by binding a labelling agent either directly or indirectly to a substance C which reacts with said monoclonal antibody, and a labelled substance D prepared by binding a labelling agent either directly or indirectly to a substance D which reacts with said substance B, to said different reaction areas, respectively, to allow for said monoclonal antibody and said substance B to react with said labelled substance C and said labelled substance D, respectively, (e) washing said carrier to remove said monoclonal antibody, said substance B, said labelled substance C, and said labelled substance D, which failed to directly or indirectly bind to said immobilized specimen, (f) measuring signal intensities y and x of said labelling agents of said labelled substance C and said labelled substance D, which had been bound to said immobilized specimen, respectively, and (g) determining the presence or absence of the uterine endometrial cancer cell in the specimen by evaluating the signal intensity y indicated by the labelling agent of said labelled substance C in relation to the signal intensity x indicated by the labelling agent of said labelled substance D.

This method may be referred to as Assay method II in the following description.

BRIEF DESCRIPTION OF THE DRAWINGS

FIGS. 2(a), 2(b), 2(c), 2(d), 2(e), 2(f) and 2(g) are diagrams showing results obtained by measuring five specimens of normal uterine endometrial cells and two specimens of uterine endometrial cancer cells using MSN-1 antibody and the anti-actin antibody.

FIGS. 3(a), 3(b) and 3(c) are diagrams showing distribution of measurements independently for uterine endometrial cell specimens from 14 normal cases, five uterine benign disease cases, and four uterine endometrial cancer cases.

DETAILED DESCRIPTION OF THE INVENTION

Figure 1:
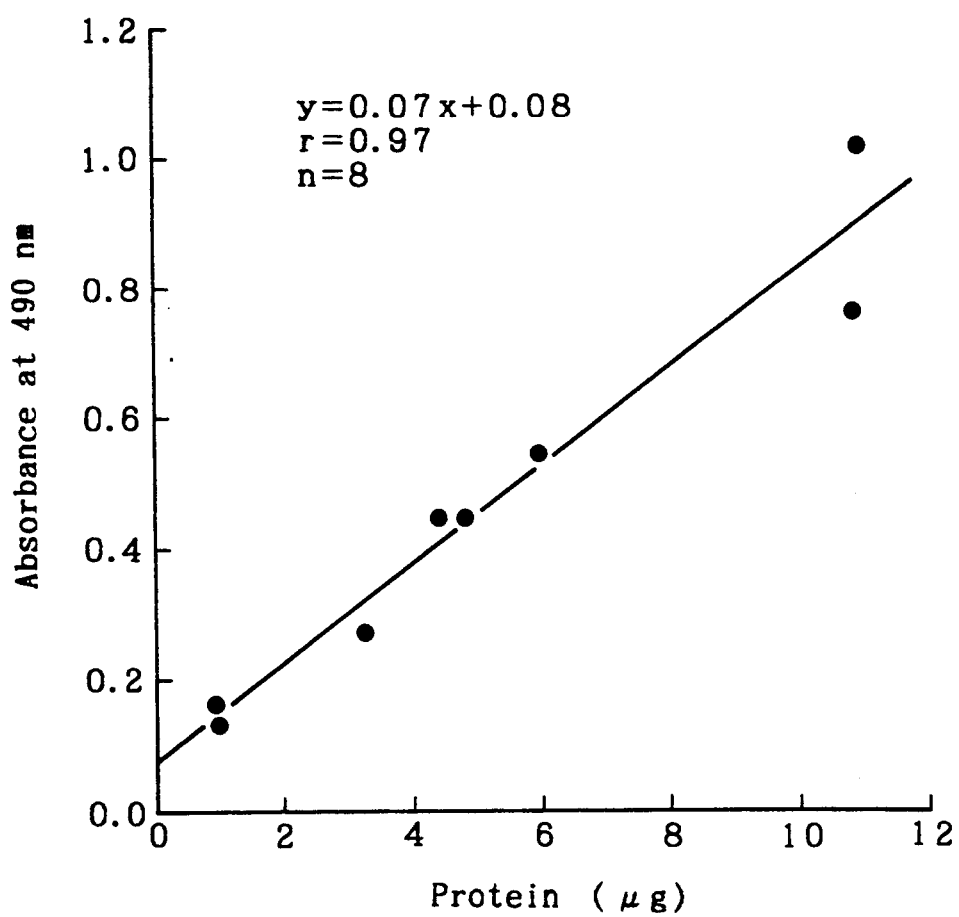
FIG. 1 is a diagram showing correlation between results obtained by measuring specimens using an anti-actin antibody and protein contents of the same specimens.
Figure 2A:
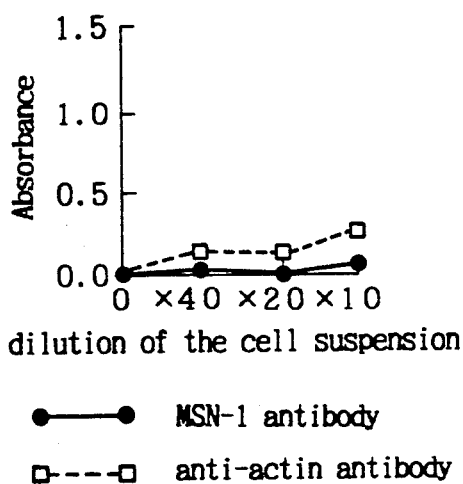
Figure 2B:
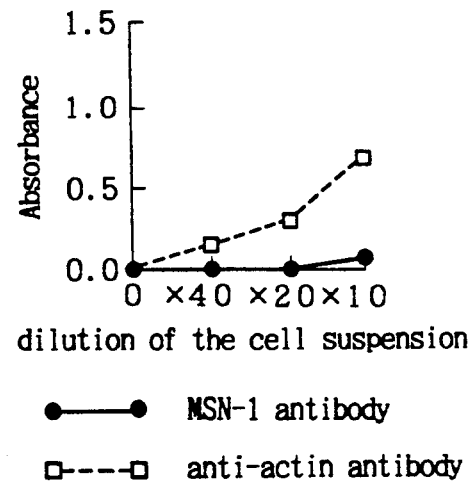
Figure 2C:
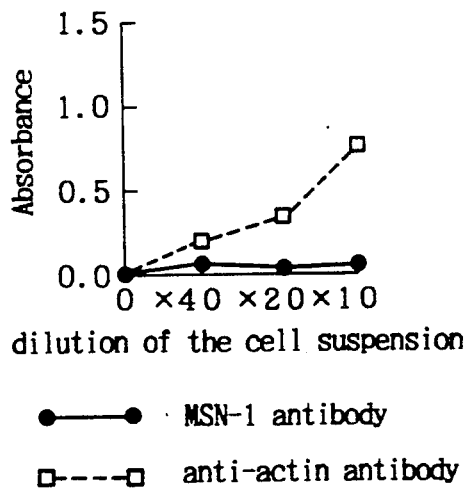
Figure 2D:
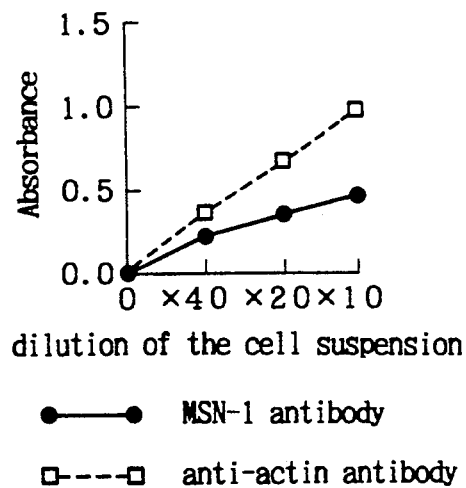

The present invention is hereinafter described in detail.

First, various materials and substances which are employed in the process of the present invention are described.

Monoclonal Antibody Immunoreactive to Uterine Endometrial Cancer Cell

A monoclonal antibody having a highly specific immunoreactivity to a human uterine endometrial cancer cell is used in the process of the present invention. Non-limiting, preferred examples of such an antibody include monoclonal antibody, MSN-1 reported in Nozawa et al., Acta Obst. Gynaec. Jpn., 39, 559–566, 1987, and monoclonal antibody, MSN-3 presented at the Eighth Meeting of the Human Cell Research Society (see Hasegawa et al., Abstracts of the Eighth Meeting of the Human Cell Research Society, 3 (Suppl.), 67, 1990).

The monoclonal antibody, MSN-1 (hereinafter simply referred to as MSN-1) has been prepared as described below.

Production of MSN-1

Cell line SNG-II from uterine endometrial adenocarcinoma of well-differentiated type was administered intraperitoneally three times at intervals of two weeks into a Balb/c mouse. Three days after the last administration, spleen cells were taken out and fused with myeloma cells of P3X63Ag8 cell line to produce hybridomas. By utilizing reactivity to uterine endometrial tissue sections from normal and endometrial cancer cases as an index, the hybridomas were cloned to choose a hybridoma clone producing an antibody which reacts only with the uterine endometrial cancer tissue at a high rate. This hybridoma clone was cultured to produce the monoclonal antibody in a culture medium, and the culture medium was salted out with 60% saturated ammonium sulfate, and the precipitate was subjected to gel filtration chromatography with Ultrogel AcA22 (IBF Biotechnics) to purify the MSN-1. The thus purified MSN-1 was examined for its immunoglobulin subclass by an immunodiffusion technique using an agarose gel. The immunoglobulin subclass of the MSN-1 was confirmed to be IgM.

The inventors of the present invention have deposited the MSN-1-producing hybridoma in Fermentation Research Institute on Mar. 22, 1991 (FERM P-12126: transferred to International Deposit No. BP-3784).

The thus produced MSN-1 was examined for its reactivity with different types of uterine endometrial tissue lesions by immunohistochemical staining using formalin fixed sections. It was then confirmed that only a few normal endometrial tissues are slightly stained in its luminal surface of normal endometrial glands, while more than 90% of the lesional tissues of uterine endometrial cancer are stained. Also, the rate of the positive cases wherein the tissue is stained is higher in well-differentiated types compared to poorly-differentiated types to indicate that the reactivity of the MSN-1 with the adenocarcinoma tissue is increased in proportion to the degree of histological differentiation of the endometrial adenocarcinoma. Furthermore, in endometrial hyperplasia, which is considered to be a so called precancerous lesion, the positive rate is likely to increase in accordance with the increase in the degree of morphological atypia, indicating that antigen recognized by the MSN-1 would increase with the canceration of the uterine endometrial tissue. It was also confirmed that the antigen recognized by the MSN-1 is a neutral glycolipid in the uterine endometrial cancer cell (see Iwamori, M. et al., J. Biochem., 105, 718, 1989).

The monoclonal antibody, MSN-3 (hereinafater simply referred to as MSN-3) has been prepared as described below.

Production of MSN-3

By using cell line HEC-108 from uterine endometrial adenocarcinoma of poorly-differentiated type as an immunogen, a Balb/c mouse was immunized in the same manner as the MSN-1. Spleen cells taken out of the immunized mouse were then fused with myeloma cells (SP-2) to produce hybridomas. The thus produced hybridomas were cloned to choose a hybridoma clone producing an antibody which reacts at a high rate with uterine endometrial adenocarcinoma tissues of poorly-differentiated type (differentiation degree, G3) and moderately-differentiated type (differentiation degree, G2). This hybridoma clone was then cultured to produce the monoclonal antibody in a culture supernatant, and the culture supernatant was salted out with 50% ammonium sulfate. The precipitate was subjected to affinity chromatography with Protein-A Cellulofine (Seikagaku Corp.) to purify the MSN-3. The immunoglobulin subclass of the MSN-3 was confirmed to be $IgG_1$. The MSN-3 was also measured for its reactivity with the endometrial cancer tissue. The part which indicated a high reactivity corresponded to the part showing a low degree of histological differentiation to indicate that the MSN-3 recognizes a surface antigen of the adenocarcinoma cell of the poorly-differentiated type in contrast to the MSN-1 (see, Hasegawa et al., Abstracts of the Eighth Meeting of the Human Cell Research Society, 3 (Suppl.), 67, 1990, supra).

The inventors of the present invention have deposited the MSN-3-producing hybridoma in Fermentation Research Institute on Mar. 22, 1991 (FERM P-12125: transferred to International Deposit No. BP-3783).

Substance A

Substance A which is measured in the process of the present invention is a substance which is generally present in human cells. The substance A should be generally present in cells in a sufficient amount. It is also required that the substance A is relatively stable in various treatments and it can be assayed by means of an immunoreaction or a nucleic acid hybridization. Typical examples of the substance A include substances forming cell skeleton such as actin, myosin, and tubulin; intranuclear substances such as chromatin, histone, nuclear matrix, DNA, and RNA; and cell membrane components such as $\beta_2$-microglobulin. The substance A may most preferably be actin.

Substance B

Substance B which is used in the process of the present invention is a substance which reacts with the substance A, substance B may typically be an antibody against the substance A. When the substance A is a nucleic acid such as DNA and RNA, the substance B may be an antibody against the substance A or a nucleic acid having a sequence complementary to the substance A.

When the substance B is an antibody, it may be either a polyclonal or a monoclonal antibody, and may be prepared by using an appropriate immunogen in accordance with a known technique, for example, the one described in "Methods in Immunological Experiments I to IX", edited by Japan Immunology Society, 1980. It may also be commercially purchased.

When the substance B is a nucleic acid having a sequence complementary to the substance A, it may be chemically synthesized. It may also be synthesized by PCR (polymerase chain reaction) method, or in accordance with, for example, Toyozo Takahashi, "DNA probe II, new techniques and developments", CMC Inc., 1990, to produce a nuclear acid probe from human cells.

Substance C

Substance C is a substance which reacts with the above-mentioned monoclonal antibody which has a highly specific immunoreactivity to the human uterine endometrial cell. The substance C may be, for example, an antibody against said monoclonal antibody, which is a so called secondary antibody, which may typically be an anti-immunoglobulin antibody and protein A. When the substance C is a secondary antibody, it may be either a polyclonal or a monoclonal antibody, and may be prepared by using an appropriate immunogen in accordance with a known technique such as the one described in "Methods in Immunological Experiments I to IX", edited by Japan Immunology Society, 1980, supra. It may also be commercially purchased.

Substance D

Substance D is a substance which reacts with the substance B. When the substance B is an antibody, the substance D may be an antibody against the antibody of the substance B, which is the so called secondary antibody, and may typically be an immunoglobulin and protein A. When the substance B is a nucleic acid, the substance D may be a nucleic acid having a sequence which is complementary to the substance B, said substance D binding to the substance B at a part other than the part in the substance B where the sequence is complementary to the sequence of the substance A. When the substance B is a nucleic acid, the substance D may also be an antibody against a DNA-DNA complex, an RNA-DNA complex, or an RNA-RNA complex. Furthermore, when the substance B is a substance to which a sulfone group, dinitrophenyl group, or digoxigenin has been bound to, the substance D may be an antibody against such a moiety of the substance B.

When a nucleic acid having a sequence complementary to the substance B is used as the substance D, the substance B must comprise a part including a sequence complementary to the substance A and a part including a sequence which is not complementary to the substance A.

When the substance D is an antibody, it may be either a polyclonal or a monoclonal antibody, and may be prepared by using an appropriate immunogen in accordance with a known technique such as the one described in "Methods in Immunological Experiments I to IX", edited by Japan Immunology Society, 1980, supra. It may also be commercially purchased.

When the substance D is a nucleic acid having a sequence complementary to the substance B, it may be chemically synthesized. It may also be synthesized by PCR (polymerase chain reaction) method, or in accordance with, for example, Toyozo Takahashi, "DNA probe II, new techniques and developments", CMC Inc., 1990, supra to produce a nuclear acid probe from human cells.

The substance D may comprise the same substance as the substance C when both the substances C and D are the so called secondary antibody.

The above-mentioned protein A is a substance which specifically reacts with the Fc fragment of the immunoglobulin although it is not an antibody. The protein A, therefore, may be used as the substance C or D in the process of the invention.

Labelling Agent

The labelling agent used in the process of the present invention may typically be an enzyme, a chemiluminescent reagent, a fluorescent reagent, and a radioisotope. Typical enzymes are horseradish peroxidase, alkaline-phosphatase, $\beta$-galactosidase, luciferase, glucose-6-phosphate dehydrogenase (G6PDH), glucose dehydrogenase (GDH), and the like. Typical chemiluminescent reagents are luminol, isoluminol, an acridinium ester, a dioxethan, and the like. Typical fluorescent reagents are fluorescein isothiocyanate, umbelliferone, chelates of a rare earth metal, and the like. Typical isotopes are $^{125}I$ $^{14}C$ and the like In the process of the present invention, the labelling agent is directly or indirectly bound to the monoclonal antibody having a highly specific immunoreactivity to the human uterine endometrial cancer cell, the substance B, the substance C, or the substance D. The labelling agent bound to the substance B may desirably be the same as the labelling agent which is bound to the anti-endometrial cancer monoclonal antibody, and the labelling agent bound to the substance D may desirably be the same as the labelling agent bound to the substance C.

When the labelling agent is directly bound, the labelling agent may desirably have introduced therein a functional group which is capable of binding to the monoclonal antibody having a highly specific immunoreactivity to the human uterine endometrial cancer cell, the substance B, the substance C, or the substance D. When the labelling agent is indirectly bound, avidin-biotin and BSA, for example, may be present between the labelling agent and the monoclonal antibody having a highly specific immunoreactivity to the human uterine endometrial cancer cell, the substance B, the substance C, or the substance D.

The labelling agent may be bound to the monoclonal antibody having a highly specific immunoreactivity to the human uterine endometrial cancer cell, the substance B, the substance C, or the substance D in accordance with a known technique such as the one described in "Enzyme Immunoassay, version 3", edited by Eiji Ishikawa et al., Igaku Shoin, 1987, "Methods in Immunological Experiments I to IX", edited by Japan Immunology Society, 1980, supra, or Toyozo Takahashi, "DNA probe II, new techniques and developments", CMC Inc., 1990, supra. The method utilizing the avidin and biotin (ABC method) is described in detail in Hsu, S. et al., J. Histochem. Cytochem., 29, 577, 1981.

Specimen

Specimen used in the process of the invention may be non-disrupted or disrupted cells or tissue collected from uterine cavity.

The specimen collected from the uterine cavity may be used as collected without disruption. The specimen, however, may be disrupted when a solid component such as a tissue is included in the specimen by dispersing the cells with an enzyme such as trypsin or collagenase, or by ultrasonically dispersing or disrupting the cells. The specimen may also be solubilized using a surfactant, an acid, an alkaline, or an organic solvent either alone or in combination.

When the specimen is contaminated with a large amount of erythrocytes, and peroxidase is used as the labelling agent, a non-specific reaction may be induced by the peroxidase contained in the erythrocytes. In such a case, the specimen may be subjected to hemolysis by treating the specimen with a hemolyzing agent such as ammonium chloride, or alternatively, the specimen may be treated with an excess amount of hydrogen peroxide to irreversibly inhibit the peroxidase activity originating from the erythrocytes before using the specimen.

The specimen may be collected by an ordinary clinically adopted technique, such as aspiration with an endometrium aspirating tube, or brushing with Endo-cyte (Sankyo), Endosearch (Anne Co., Ltd.), or an endometrial brush.

Carrier

The carrier employed in the present invention is not particularly limited in its material or configuration so long as the non-disrupted or disrupted uterine endometrial cells or tissues are capable of becoming physically or chemically bound to the carrier to become insolubilized and immobilized on the carrier. Exemplary carriers include those commonly used in immunoassays such as a plate, a tube, a bead, and a membrane of polyethylene, polystyrene, polypropylene, glass, nitrocellulose and nylon.

Next, the process for immunochemically detecting the uterine endometrial cancer cell using the above-described materials and substances is described in detail.

Assay Method I

First, assay method I in accordance with first embodiment of the present invention is set forth.

The immunochemical detection according to the first embodiment of the present invention comprises the steps of (a) preparing a specimen by collecting endometrial cells and/or endometrial tissue from the cavity of the uterus, and optionally disrupting the thus collected cells and/or the tissue, (b) immobilizing a predetermined amount of said specimen on two or more reaction areas on one or more carriers, (c) adding a labelled monoclonal antibody prepared by binding a labelling agent either directly or indirectly to a monoclonal antibody against the uterine endometrial cancer cell, and a labelled substance B prepared by binding a labelling agent either directly or indirectly to a substance B which is reactive to a substance A which is generally present in human cells, to different reaction areas onto which said specimen had been immobilized, respectively, to allow for said immobilized specimen to react with said labelled monoclonal antibody and with said labelled substance B, respectively, (d) washing said carrier to remove said labelled monoclonal antibody and said labelled substance B which failed to bind to said immobilized specimen, (e) measuring signal intensities y and x of said labelling agents of said labelled monoclonal antibody and said labelled substance B, which had been bound to said immobilized specimen, respectively, and (f) determining presence or absence of the uterine endometrial cancer cell in the specimen by evaluating the signal intensity y indicated by the labelling agent of said labelled monoclonal antibody in relation to the signal intensity x indicated by the labelling agent of said labelled substance B.

In the step (a) wherein the specimen is prepared by collecting endometrial cells and/or endometrial tissue from the cavity of the uterus, and optionally disrupting the thus collected cells and/or the tissue, the specimen collected as described above is adjusted so that the specimen is ready for use in the assay by optionally subjecting the collected specimen to necessary treatments.

In the step (b) wherein a predetermined amount of the thus prepared specimen is immobilized on two or more reaction areas on one or more carriers, the specimen is either physically or chemically immobilized on the carrier.

When the carrier onto which the specimen is immobilized is a plate or a membrane, the specimen may be immobilized onto a plurality of reaction areas on one piece of the carrier. When a tube or a bead is used as the carrier, the specimen may be immobilized on two or more pieces of the carrier so that the amount of the specimen immobilized on each piece of the carrier would be the same.

In the process of the invention, two or more reaction areas on one or more carriers are required since two types of assays, namely, the assay utilizing the antibody against the uterine endometrial cancer cell, and the assay utilizing the substance B which reacts with the substance A which is generally present in human cells are carried out for one specimen, so that the results obtained in the two assays may be compared.

In the process of the invention, it is more preferable to immobilize the specimen on a plurality of reaction areas on one carrier, namely, to provide both the reaction area for the assay utilizing the antibody against the uterine endometrial cancer cells and the reaction area for the assay utilizing the substance B on the same carrier, since the reaction conditions in the plurality of reaction areas may more readily be made uniform.

The term "reaction area" used herein designates an area wherein the reaction may independently take place without being influenced by the reactions in other areas. When a microtiter plate is used for the carrier, such a reaction area corresponds to an individual well. When a membrane or a plate such as a slide glass is used for the carrier, such a reaction area corresponds to an area separated by a sufficient distance from the adjacent reaction area, or an area surrounded by a border, wherein the reaction solution in the area is prevented from being mixed with the reaction solution in another area.

The specimen may be immobilized on the carrier, for example, by directly coating a predetermined amount of the specimen on the predetermined area of the carrier followed by air drying; or by suspending the specimen in an appropriate buffer solution such as physiological saline or phosphate-buffered buffered saline, and dispensing an aliquot of the suspension to the predetermined area of the carrier followed by an incubation at 4° to 60° C. for 0.5 to 24 hours, preferably at 37° to 60° C. for 0.5 to 2 hours to physically adsorb the specimen onto the carrier. The specimen may also be immobilized by suspending the specimen in a solvent such as methanol, and dispensing an aliquot of the suspension to the predetermined area of the carrier, and evaporating the medium at 20° to 100° C., preferably at 50° to 90° C.

The next step (c) wherein the labelled monoclonal antibody prepared by binding a labelling agent either directly or indirectly to the monoclonal antibody against the uterine endometrial cancer cell, and the labelled substance B prepared by binding a labelling agent either directly or indirectly to the substance B which is reactive to the substance A generally present in human cells are respectively added to different areas of the reaction areas onto which said specimen had been immobilized to allow for said immobilized specimen to react with said labelled monoclonal antibody and with said labelled substance B, respectively, may desirably be carried out under appropriate reaction conditions.

More illustratively, when the reaction between the specimen and the labelled monoclonal antibody and the reaction between the specimen and the labelled substance B are antigen-antibody reactions, this step (c) may be carried out under the conditions of about 4° to 37° C. for about 0.5 to 24 hours, and more preferably at about 20° to 37° C. for about 0.5 to 2 hours. When the substance B is a nucleic acid, the reaction between the specimen and the substance B may preferably be carried out at 20° to 65° C. for about 2 to 24 hours. In the latter case, the reaction conditions including the temperature and the reaction period may be appropriately selected in accordance with the number of bases included in the substance B.

The step (d) wherein said carrier is washed to remove said labelled monoclonal antibody and said labelled substance B which failed to bind to said immobilized specimen may typically be carried out using water, physiological saline, a buffer solution such as phosphate-buffered saline and Tris-HCl buffer which had been adjusted to approximately neutral pH, or any of the above-mentioned solutions having a surfactant such as Tween 20 added thereto. When the substance B is a nucleic acid, the step of removing the labelled substance B which failed to bind to the specimen may be carried out by washing the carrier with a commonly employed solution such as SSC (standard saline citrate, 0.15M sodium chloride / 0.015M sodium citrate).

The step (e) wherein signal intensities y and x of said labelling agents are respectively measured for the labelled monoclonal antibody and for the labelled substance B which had been bound to said immobilized specimen may be carried out as described below in accordance with the type of the labelling agent employed.

When the labelling agent employed is an enzyme, activity of the enzyme is measured, and when the labelling agent is a fluorescent reagent, intensity of the fluorescence is measured. When the labelling agent is a chemiluminescent reagent, intensity of the luminescence is measured, and when the labelling agent is a radioisotope, radioactivity is measured. The measurements are physically carried out either quantitatively or qualitatively by using such measurement equipment as a Photometer, a reflection meter, a fluorometer, a luminometer, and a scintillation counter.

When the labelling agent employed is an enzyme, a substrate is used for measuring the enzyme activity. The substrate employed is not limited so long as the substrate allows for the enzyme-substrate reaction to be quantitatively promoted corresponding to the quantity of the enzyme present, and the quantity of the reaction product or the quantity of the substrate decreasing in the reaction or remaining after the reaction may be easily measured. For example, when the labelling agent is peroxidase, the substrate employed may be tetramethylbendidine-$H_2O_2$, o-phenylenediamine-$H_2O_2$, 5-aminosalicylic acid-$H_2O_2$, and the like. When the labelling agent is alkaline phosphatase, the substrate employed may be, for example, toluidine salt of 5-bromo-4-chloro- 3-indolylphosphate. When the enzyme is $\beta$-galactosidase, the substrate employed may be, for example, p-nitrophenyl-$\beta$-D-galactopylanoside.

In consideration of the capability of a qualitative determination with the naked eye of the quantity of the labelling agent in the labelled substance which had been bound to the specimen, a preferred measurement system is a system wherein the labelled substance includes an enzyme such as peroxidase, alkaline phosphatase, or $\beta$-galactosidase as the labelling agent, and wherein an increase in quantity of the enzyme reaction product may be determined by means of a color development.

In the process according to the first embodiment of the present invention, the presence or the absence of the uterine endometrial cancer cell in the specimen is determined by evaluating the two types of measurements obtained in the preceding steps (a) to (e), namely, by evaluating the signal intensity y of the labelling agent of said labelled monoclonal antibody indicated in one reaction area in relation to the signal intensity x of the labelling agent of said labelled substance B indicated in another reaction area.

More illustratively, the measurements obtained may be evaluated by (1) calculating the ratio of the signal intensity y indicated by the labelling agent of said labelled monoclonal antibody to the signal intensity x indicated by the labelling agent of said labelled substance B, comparing the ratio with a preliminarily determined reference ratio, that is, a cut off value, and determining the specimen whose ratio is larger than the cut off value as positive, or (2) comparing the signal intensity y indicated by the labelling agent of said labelled monoclonal antibody with the signal intensity x indicated by the labelling agent of said labelled substance B, and determining the specimen showing the signal intensity y larger than the signal intensity x as positive.

In the evaluation process (1), the reference ratio, that is, the cut off value may be set by measuring the signal intensity x and the signal intensity y, for the specimens collected from normal, benign disease, and cancer cases as described above, calculating the ratio of the signal intensity y to the signal intensity x, and determining the cut off value on the bases of the distribution of the ratio by statistical means. The cut off value may also be set appropriately in terms of clinical utility.

The evaluation process (2) may typically be carried out by using an enzyme for the labelling agent to constitute a measurement system wherein the result of the measurement is indicated by an enzyme reaction accompanied by a color development to enable a qualitative evaluation of the results with the naked eye. More illustratively, the quantity of the specimen and the quantities of the labelled substance B and the labelled monoclonal antibody are respectively adjusted so that the above mentioned reference ratio would be approximately 1, and the color development, namely, the signal intensity y corresponding to the quantity of the labelled monoclonal antibody is compared with the color development, namely, the signal intensity x corresponding to the quantity of the labelled substance B, to determine the specimen showing the color development (signal intensity y) stronger than the reference color development (signal intensity x) as positive with regard to the presence of the uterine endometrial cancer cell.

In the first embodiment of the present process, the quantity of the labelled substance B is an index for the total cell number included in the specimen.

Referring to FIG. 1, there is shown a correlation between the signal intensity x, which is the absorbance at a wave length of 490 nm measured in accordance with the first embodiment of the present invention, indicating the quantity of the labelled substance B which had been bound to the specimen, and the quantity of protein included in the same specimen measured in accordance with a technique described in Lowry, O. H. et al., Jo Biol. Chem., 193, 265, 1951, after solubilizing the specimen with 0.1N sodium hydroxide solution. In the measurement, horseradish peroxidase-labelled anti-acitin antibody was used for the labelled substance B. The substrate for the enzyme was o-phenylenediamine-$H_2O_2$.

Regression line was represented by $y = 0.07 \times + 0.08$, and correlation coefficient r was 0.97, to indicate that the quantity of the labelled substance B is proportional to the protein quantity in the specimen, and therefore, the quantity of the labelled substance B may be used as an index for the total cell number included in the specimen.

Assay Method II

The immunochemical detection according to the second embodiment of the present invention comprises the steps of (a) preparing a specimen by collecting endometrial cells and/or endometrial tissue from the cavity of the uterus, and optionally disrupting the thus collected cells and/or the tissue, (b) immobilizing a predetermined amount of said specimen on two or more reaction areas on one or more carriers, (c) adding a monoclonal antibody against the uterine endometrial cancer cell and a substance B which is reactive to a substance A which is generally present in human cells to different areas of said reaction areas onto which said specimen had been immobilized to allow for said immobilized specimen to react with said monoclonal antibody and with said substance B, respectively, (d) adding a labelled substance C prepared by binding a labelling agent either directly or indirectly to a substance C which reacts with said monoclonal antibody, and a labelled substance D prepared by binding a labelling agent either directly or indirectly to a substance D which reacts with said substance B, to said different reaction areas, respectively, to allow for said monoclonal antibody and said substance B to react with said labelled substance C and said labelled substance D, respectively, (e) washing said carrier to remove said monoclonal antibody, said substance B, said labelled substance C and said labelled substance D which failed to directly or indirectly bind to said immobilized specimen, (f) measuring signal intensities y and x of said labelling agents of said labelled substance C and said labelled substance D, which had been bound to said immobilized specimen, respectively, and (g) determining the presence or absence of the uterine endometrial cancer cell in the specimen by evaluating the signal intensity y indicated by the labelling agent of said labelled substance C in relation to the signal intensity x indicated by the labelling agent of said labelled substance D.

The steps (a) and (b) are similar to those carried out in the process according to the first embodiment of the present invention, and therefore, are not described any further.

The next step (c) wherein the monoclonal antibody against the uterine endometrial cancer cell and the substance B which is reactive to the substance A which is generally present in human cells are respectively added to different reaction areas onto which said specimen had been immobilized to allow for said immobilized specimen to react with said monoclonal antibody and with said substance B, respectively, may desirably be carried out under appropriate reaction conditions.

More illustratively, when the reaction between the specimen and the monoclonal antibody and the reaction between the specimen and the substance B are antigen-antibody reactions, this step (c) may be carried out under the conditions of about 4° to 37° C. for about 0.5 to 24 hours, and more preferably at about 20° to 37° C. for about 0.5 to 2 hours. When the substance B is a nucleic acid, the reaction between the substance B and the substance A may preferably be carried out at 20° to 65° C. for about 2 to 24 hours. In the latter case, the reaction conditions including the temperature and the reaction period may be appropriately selected in accordance with the number of bases included in the substance B.

The step (d) wherein the labelled substance C prepared by binding a labelling agent either directly or indirectly to the substance C which reacts with said monoclonal antibody, and the labelled substance D prepared by binding a labelling agent either directly or indirectly to the substance D which reacts with said substance B are respectively added to the different reaction areas to allow for said monoclonal antibody and said substance B to react with said labelled substance C and said labelled substance D, respectively, also, may desirably be carried out under appropriate reaction conditions.

More illustratively, when the reaction between the monoclonal antibody and the labelled substance C and the reaction between the substance B and the labelled substance D are antigen-antibody reactions, this step (d) may be carried out under the conditions of about 4° to 37° C. about for 0.5 to 24 hours, and more preferably at about 20° to 37° C. for about 0.5 to 2 hours. When the substance D is a nucleic acid, the reaction between the the substance D and the substance B may preferably be carried out at 20° to 65° C. for about 2 to 24 hours. In the latter case, the reaction conditions including the temperature and the reaction period may be appropriately selected in accordance with the number of bases included in the substance D.

The step (e) wherein the carrier is washed to remove the monoclonal antibody, the substance B, the labelled substance C and the labelled substance D which failed to directly or indirectly bind to said immobilized specimen may typically be carried out using water, physiological saline, a buffer solution such as phosphate-buffered saline and Tris-HCl buffer which had been adjusted to approximately neutral pH, or any of the above-mentioned solutions having a surfactant such as Tween 20 added thereto. When the substance B and the substance D are nucleic acids, the step of removing the labelled substance B which failed to bind to the specimen and the labelled substance D which failed to bind to the labelled substance B may preferably be carried out by washing the carrier with a commonly employed solution such as SSC.

In the process according to the second embodiment of the present invention, this washing step (e) may be carried out in a single step. However, this washing step (e) may more typically comprise two different steps, namely, the step for removing the monoclonal antibody and the substance B which failed to directly bind to the specimen, and the step for removing the labelled substance C and the labelled substance D which failed to indirectly bind to the specimen with the intervening monoclonal antibody or the substance B.

The step (f) wherein the signal intensities x and y of the labelling agents are respectively measured for the labelled substance D and the labelled substance C which had been bound to said immobilized specimen may be carried out as described above for the process according to the first embodiment of the invention in accordance with the type of the labelling agent employed.

In the process according to the second embodiment of the invention, the presence or the absence of the uterine endometrial cancer cell in the specimen may be determined by evaluating the two types of measurements obtained in the preceding steps (a) to (f).

The evaluation of the two types of measurements may be carried out in a similar manner as the process according to the first embodiment of the present invention to determine the presence or the absence of the uterine endometrial cancer cell in the specimen.

It should be noted that, in the process according to the second embodiment of the present invention, the above-described steps may not necessarily be carried out in the above-described order. The washing step (e), as mentioned above, may be carried out in two steps, and in such a case, the washing steps may be carried out after the step (c) and after the step (d), respectively. In addition, the substances added in the step (d) may be preliminarily mixed with the substances added in the step (c) to form a complex of the monoclonal antibody and the labelled substance C and a complex of the substance B and the labelled substance D, and then, the thus formed complexes may be added to the specimen immobilized in the steps (a) and (b).

The processes according to the first and the second embodiment of the present invention, namely, Assay method I and Assay method II respectively have the merits as described in (i) and (ii) below.

(i) Assay Method I

In the Assay method I, the labelling agent is bound to the cancer cell-specific antibody, and to the substance B reactive to the substance A. Therefore, the assay may be carried out without requiring secondary materials such as the substances C and D, which may typically be a secondary antibody, and the assay requires fewer reaction steps and shorter reaction period.

(ii) Assay method II

In the Assay method II, the labelling agent is bound to the substance C reactive to the cancer cell-specific antibody, and to the substance D reactive to the substance B. Since the cancer cell-specific antibody and the substance B are not labelled with the labelling agent, there is no risk of deteriorating the activity of the cancer cell-specific antibody or the substance B by the labelling. For the purpose of simplifying the assay procedure, the labelled substance C may preferably be the same as the labelled substance D, and in such a case, only one labelling step is required in the assay. Moreover, sensitivity of the assay by the Assay method II is higher than that of the assay by the Assay method I owing to the use of the labelled secondary substance. Therefore, the Assay method II may be carried out by using a smaller amount of the sample specimen than the Assay method I.

The process according to the present invention may be carried out as described above. It is to be noted that, although the present process is limited to an immunochemical detection of the uterine endometrial cancer cell, it may be applied to an immunochemical detection of uterine cervical carcinoma cell and an immunochemical detection of a pulmonary cancer cell in sputum, if a hybridoma producing an appropriate monoclonal antibody were obtained.

The present invention is hereinafter described in detail by referring to Examples, which by no means limit the scope of the invention.

EXAMPLES

Example 1

Measurement of Specimens by Enzyme Immunoassay (1)

(1) Preparation and immobilization of specimen

Uterine endometrial cells were collected with Endosearch (Anne Co., Ltd.) by brushing. The cells were suspended in 2 ml of physiological saline. The suspension was centrifuged at 1,500 rpm for 10 minutes with a centrifuge, CD 50SR (Tomy Seiko Co., Ltd.), and the supernatant was removed. The precipitate was suspended in 500 µl of methanol to prepare a cell suspension.

When the collected cell specimen had been significantly contaminated with blood, the cell suspension in the physiological saline was centrifuged to remove the supernatant, and 1ml of 0.8% ammonium chloride/ 0.1% potassium hydrogencarbonate/ 0.037% tetrasodium ethylenediaminetetraacetic acid solution, pH 7.2 was added to the precipitate. The mixture was allowed to stand for one minute to promote hemolysis, and then centrifuged at 2,000 rpm for two minutes with a centrifuge, MC 150(Tomy Seiko Co., Ltd.). The supernatant was removed, and the precipitate was suspended in 500 µl of methanol to prepare a cell suspension.

Next, the cell suspension was disrupted with sonicator (Ohtake Works) for five seconds with ice cooling. This procedure was repeated three times.

The thus treated cell suspension was diluted with methanol to 10, 20 and 40-fold volumes. Each of the diluted suspensions were dispensed in 50 µl aliquots into four wells of a 96-well microtiter plate (Nippon InterMed K. K.). The microtiter plate was then baked in an oven (Toyo Seisakusyo Co., Ltd.) at 80° C. for 10 minutes to dry the microtiter plate by evaporating the solvent and to thereby immobilize the cell specimen in the wells of the microtiter plate. After baking, the microtiter plate was cooled for at least 10 minutes in an ice bath.

Next, 100 µl of 0.3% hydrogen peroxide solution was added to each well, and the mixture was allowed to stand for 30 minutes in order to inhibit the activity of peroxidase, whose source of contamination is erythrocytes. The microtiter plate was then washed with deionized water for three times.

(2) Measurement by enzyme immunoassay

A 2 µg/ml solution of monoclonal antibody, MSN-1 (hereinafter simply referred to as MSN-1), a 100-fold dilution of monoclonal anti-actin antibody (class IgM, Advance Co., Ltd., hereinafter simply referred to as anti-actin antibody), and a 500-fold dilution of goat anti-mouse IgM antibody (TAGO Inc.) labelled with horseradish peroxidase (hereinafter abbreviated as HRPO) were prepared by using 5% bovine serum albumin (hereinafter abbreviated as BSA) in 76 mM phosphate-buffered saline pH 6.4 (hereinafter abbreviated as PBS). The HRPO-labelled goat anti-mouse IgM antibody dilution was mixed with an equal volume of the MSN-1 solution, and with an equal volume of the anti-actin antibody solution, respectively, and 100 µl aliquot of either of the resulting mixtures was added to the wells of the microtiter plate prepared in the above (1).

After allowing to react at 25° C. for 1.5 hours, the wells of the microtiter plate were washed with 0.005% polyoxyethylene (20) sorbitan laurate/ 0.9% sodium chloride solution for five times, and with deionized water for twice.

After washing, 100 µl of 0.027% hydrogen peroxide/ 0.3% o-phenylenediamine/MacIlvaine buffer, pH 5.0 was added to the well.

After allowing to react at 25° C. for 10 minutes, 100 µl of 1N hydrochloric acid was added to the well to cease the reaction. The reaction solution was measured for its color intensity by measuring absorbance with microplate reader, NJ-2000 (Nippon InterMed K.K.) at a wave length of 490 nm by using a reference wave length of 620 nm.

FIG. 2 shows the results of the measurements wherein both the MSN-1 and the anti-actin antibody were used for 5 cases of normal uterine endometrial cells, and two cases of endometrial cancer cells. FIGS. 2(a) to 2(e) are the cases of normal uterine endometrial cells, whereas 2(f) and 2(g) are the cases of uterine endometrial cancer cells.

In the measurement of the uterine endometrial cancer cells using the MSN-1, the absorbance increased in accordance with increase in the quantity of the immobilized specimen. In the measurement of the normal uterine endometrial cells, the absorbance also increased with increase in the quantity of the immobilized specimen although the degree of the increase was smaller than the case of the uterine endometrial cancer cells. Such an increase in the absorbance with the increase in the quantity of the specimen in the assay using the MSN-1 indicates that the absorbance measured may vary in accordance with the quantity of the specimen immobilized on the carrier. Consequently, it is inadequate to determine the result as positive merely on the basis of a high absorbance.

However, FIG. 2 indicates that, if the absorbance measured in the assay using the MSN-1 is determined by referring to the absorbance measured in the assay using the anti-actin antibody, an adequate determination of the positive and negative results may be enabled.

Example 2

Comparison Between the Evaluation Methods of the Measurements

The procedure of Example 1 was repeated by using the specimens of uterine endometrial cells from 14 normal, five benign uterine disease, and four uterine endometrial cancer cases. The measurement, namely, the absorbance obtained in the assay utilizing the anti-actin antibody was designated x, whereas the measurement, namely, the absorbance obtained in the assay utilizing the MSN-1 was designated y.

The same specimens were quantitatively analyzed for protein content as described below.

Specimens for the protein quantitative analysis were prepared by adding 50 µl of PBS to 50 µl of the methanol dilution of the cell suspension prepared by repeating the procedure of Example 1 (1). Standards for the protein quantitative analysis were prepared by adding 50 µl of methanol to 50 µl of BSA solution in PBS which had been adjusted to 1 to 1,600 µg/ml. The specimens and the standards were respectively solubilized in 0.1N sodium hydroxide solution at 30° C. for 30 minutes, and measured in accordance with the method described in Lowry, O. H. et al., Jo Biol. Chem., 193, 265, 1951, supra. The protein concentration of the specimens equivalent to BSA were calculated from a calibration curve obtained from the absorbance of the BSA standard. The protein concentration of the specimen in mg/ml was designated z.

The results obtained were then evaluated in terms of the absorbance obtained by using the MSN- 1, y; ratio of the absorbance obtained by using the MSN- 1, y in relation to the protein concentration, z (i.e. y/z); and ratio of the absorbance obtained by using the MSN- 1, y in relation to the absorbance obtained by using the anti-actin antibody, x (i.e. y/x).

In the evaluation of the results, a cut off value was set for each of y, y/x, and y/z, in order to discriminate the positive and negative results by calculating a mean value+2SD (SD, standard value) for 14 specimens from normal cases in which the dilution of the cell suspension with methanol in the immobilization of the specimen was 20 folds. The cut off values were calculated to be 0.35, 1.50, and 1.10 for y, y/z, and y/x, respectively.

FIGS. 3 (a), 3(b), and 3(c) represent distribution of the y, y/x, and y/z values, respectively, for the different types of the diseases. Table 1 shows rate of the positive results determined by referring to the cut off values as determined above.

The results shown in FIG. 3 and Table 1 indicate that rate of false positive results in the normal cases and the cases of uterine benign diseases would be significantly decreased when the results are evaluated by referring to the protein concentration or the absorbance obtained by using the anti-actin antibody, compared to the evaluation solely based on the absorbance obtained by using the MSN- 1. In particular, it was indicated that, when the results are evaluated by referring to the absorbance measurements obtained by using the anti-actin antibody in accordance with the process of the present invention, namely, on the basis of the y/x value, the false positive rate in the cases of uterine benign diseases would be further decreased to verify the usefulness of the present invention.

TABLE 1

| Positive rate in the evaluations | | | |
|---|---|---|---|
| | Evaluation | | |
| | y | y/z | y/x |
| Normal | 14.3% | 0% | 0% |
| | (2/14) | (0/14) | (0/14) |
| Uterine endometrial cancer | 100% | 100% | 100% |
| | (4/4) | (4/4) | (4/4) |
| Uterine benign diseases | 80.0% | 40.0% | 20.0% |
| | (4/5) | (2/5) | (1/5) |

* The figures in the parentheses represent the number of the positive case per total number of the cases.

Example 3

Measurement of Specimens by Enzyme Immunoassay (2)

HRPO was directly bound to the MSN- 1 and the anti-actin antibody, respectively, in accordance with the method described in Nakane, P. K. et al., Histochem. Cytochem., 22, 1084, 1974. The HRPO-labelled MSN- 1 and the HRPO-labelled anti-actin antibody were diluted with 5% BSA in PBS to 3,000-and 200-fold volumes, respectively. To a microtiter plate having the specimens immobilized by the procedure of Example 1 ( 1), the HRPO-labelled MSN- 1 and the HRPO-labelled anti-actin antibody dilutions were respectively dispensed in 100 μl aliquots into two wells.

After allowing to react at 25° C. for 1.5 hours, the wells of the microtiter plate were washed with 0.005% polyoxyethylene ( 20) sorbitan laurate/ 0.9% aqueous solution of sodium chloride for five times, and with deionized water for twice.

After washing, 100 μl of 0.027% hydrogen peroxide/ 0.3% o-phenylenediamine/ MacIlvaine buffer solution, pH 5.0 was added to the well.

After allowing to react at 25° C. for 10 minutes, the reaction was ceased by adding 100 μl of 1N hydrochloric acid to the well. The reaction solution was measured for its color intensity with microplate reader, NJ- 2000 (Nippon InterMed K.K.) at a wave length of 490 nm by using a reference wave length of 620 nm.

Figure 4:
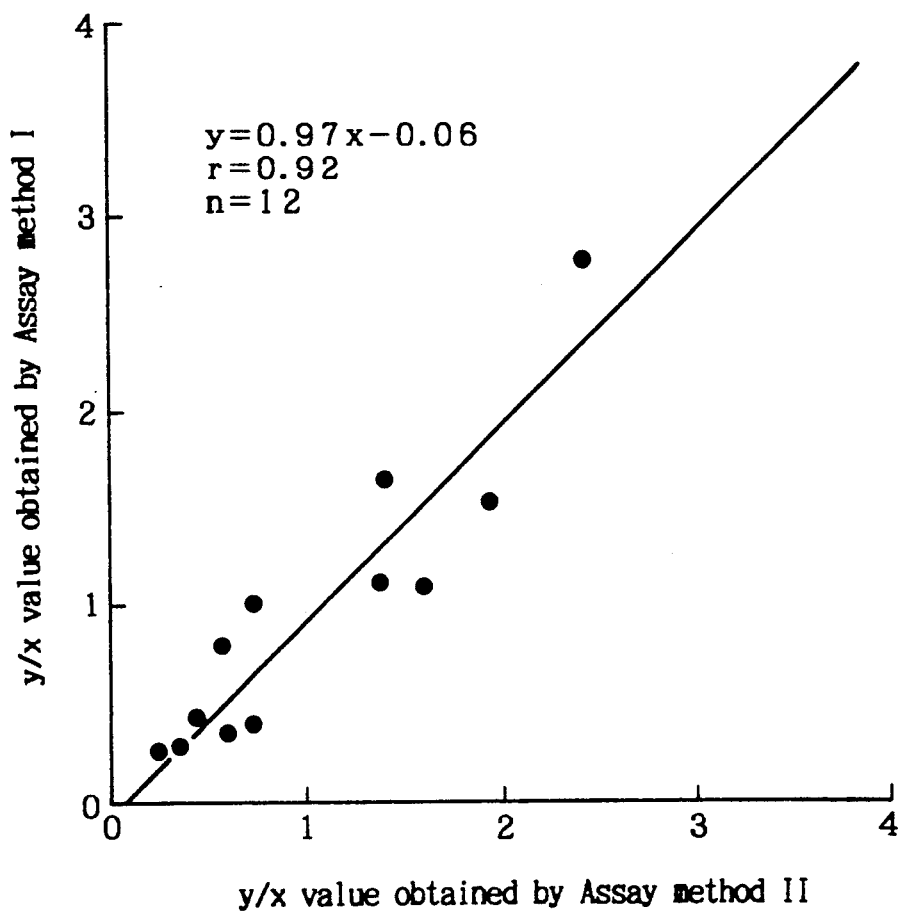
FIG. 4 is a diagram showing the correlation between the results obtained by measuring the specimens by Assay method I utilizing MSN-1 and anti-actin antibody having an enzyme directly labelled thereto, and the results obtained by Assay method II utilizing an enzyme-labelled secondary antibody.

The same specimens were measured by the assay method of this Example utilizing the MSN- 1 and the anti-actin antibody having the enzyme directly labelled thereto (Assay method I) and the enzyme immunoassay method of Example 1 ( 2) utilizing the enzyme-labelled secondary antibody (Assay method II). FIG. 4 shows correlation between the measurements, namely, the y/x values obtained by the Assay method I and the Assay method II The coefficient of the correlation was calculated to be 0.92, indicating a high correlation between the results obtained by the Assay method I and the Assay method II.

The advantages realized by the process for detecting the uterine endometrial cancer cell in accordance with the present invention may be summarized as below.

First, objectivity of the data obtained by the process of the present invention is significantly higher than that of the conventional cytodiagnosis, wherein the the positive and the negative results had been determined on the bases of subjective criteria. Also, the measurement of the present invention may not necessarily be carried out by those skilled in the art, but may be conveniently carried out by those who have not been particularly trained.

Secondly, in the process of the present invention, the quantity of the substance which is generally present in human cells is measured by the same method and under the same conditions as the measurement using the antibody against the uterine endometrial cancer cell to use the quantity as an index for the total cell number or quantity, or the quantity of the disrupted cell in the specimen, and therefore, a more accurate detection of the uterine endometrial cancer cell has been enabled by preventing determination errors due to, for example, a non-specific reaction.

Thirdly, the process of the present invention is capable of examining a large number of specimens in a short period, and may be automated. Consequently, diagnosis of the uterine endometrial cancer in group examination or mass screening may be carried out more readily to satisfy social demands.

We claim:

1. A method of screening for the presence of endometrial cancer cells in an endometrial cell specimen, comprising the steps of
    (a) preparing an endometrial cell specimen by collecting endometrial cells from the cavity of the uterus,
    (b) immobilizing a predetermined amount of said specimen on two or more reaction areas on one or more carriers, (c) contacting one of said reaction areas with a monoclonal antibody labelled with a labelling agent, wherein said monoclonal antibody specifically binds an endometrial cancer associated antigen, (d) contacting another of said reaction areas with an antibody B labelled with a labelling agent, wherein said antibody B specifically binds a substance A which is present in human cells in a substantially constant amount, (e) washing said reaction areas to remove unbound labelled monoclonal antibody and unbound labelled antibody B, and (f) measuring a signal intensity y of bound said labelled monoclonal antibody as a measure of the level of endometrial cancer associated antigen and measuring a signal intensity x of bound said labelled antibody B as a measure of the level of substance A, (g) wherein an elevated level of the endometrial cancer associated antigen relative to the level of substance A is associated with the presence of endometrial cancer cells in the endometrial cell specimen.

2. The method of screening for the presence of endometrial cancer cells in an endometrial cell specimen according to claim 1 wherein said endometrial cells are disrupted.

3. A method of screening for the presence of endometrial cancer cells in an endometrial cell specimen, comprising the steps of (a) preparing an endometrial cell specimen by collecting endometrial cells from the cavity of the uterus, (b) immobilizing a predetermined amount of said specimen on two or more reaction areas on one or more carriers, (c) contacting one of said reaction areas with a monoclonal antibody which specifically binds an endometrial cancer associated antigen, (d) contacting another of said reaction areas with an antibody B which specifically binds a substance A which is present in human cells in a substantially constant amount, (e) contacting the reaction area of step (c) with an antibody C labelled with a labelling agent, wherein said antibody C specifically binds said monoclonal antibody, (f) contacting the reaction area of step (d) with an antibody D labelled with a labelling agent, wherein said antibody D specifically binds said antibody B, (g) washing said reaction areas to remove unbound monoclonal antibody, unbound antibody B, unbound labelled antibody C and unbound labelled antibody D, and (h) measuring signal intensity y of bound said labelled antibody C as a measure of the level of endometrial cancer associated antigen and measuring a signal intensity of bound said labelled antibody D as a measure of the level of substance A, (i) wherein an elevated level of the endometrial cancer associated antigen relative to the level of substance A is associated with the presence of endometrial cancer cells in the endometrial cell specimen.

4. The method of screening for the presence of endometrial cancer cells in an endometrial cell specimen according to claim 3 wherein said endometrial cells are disrupted.

5. The method of screening for the presence of endometrial cancer cells in an endometrial cell specimen according to claim 1 or 3 wherein the signal intensity y is divided by the signal intensity x to obtain a ratio, and wherein a positive result is indicated by a ratio larger than a predetermined value.

6. The method of screening for the presence of endometrial cancer cells in an endometrial cell specimen according to claim 1 or 3 wherein substance A is selected from the group consisting of cell skeleton substances, intranuclear substances and cell membrane components.

7. The method of screening for the presence of endometrial cancer cells in an endometrial cell specimen according to claim 6 wherein substance A is selected from the group consisting of actin, myosin, tubulin, chromatin, histone, nuclear matrix, DNA, RNA, and $\beta_2$-microglobulin.

8. The method of screening for the presence of endometrial cancer cells in an endometrial cell specimen according to claim 7 wherein substance A is actin.

9. The method of screening for the presence of endometrial cancer cells in an endometrial cell specimen according to claim 1 or 3 wherein said labelling agent is an enzyme, and wherein measurement of the signal intensity is carried out by measuring the signal intensity of a substance which increases as a result of activity of said enzyme.

10. The method of screening for the presence of endometrial cancer cells in an endometrial cell specimen according to claim 1 or 3 wherein said labelling agent is selected from the group consisting of chemiluminescent reagents, fluorescent reagents, and radioisotopes.

11. The method of screening for the presence of endometrial cancer cells in an endometrial cell specimen according to claim 9 wherein the signal intensities are evaluated visually.

12. The method of screening for the presence of endometrial cancer cells in an endometrial cell specimen according to claim 3 wherein the antibody C is the same as the antibody D.

* * * * *